United States Patent
Cox et al.

(10) Patent No.: US 6,613,878 B1
(45) Date of Patent: Sep. 2, 2003

(54) PCNA BINDING SUBSTANCE

(75) Inventors: Lynne S. Cox, Summertown (GB); David P. Lane, Fife (GB); Emma Warbrick, Fife (GB); David M. Glover, Perth (GB)

(73) Assignee: Cyclacel Limited, Dundee (SC)

(*) Notice: Subject to any disclaimer, the term of this patent is extended or adjusted under 35 U.S.C. 154(b) by 0 days.

(21) Appl. No.: 08/945,645

(22) PCT Filed: May 2, 1996

(86) PCT No.: PCT/GB96/01056
§ 371 (c)(1),
(2), (4) Date: Jul. 31, 1998

(87) PCT Pub. No.: WO96/35715
PCT Pub. Date: Nov. 14, 1996

(30) Foreign Application Priority Data

May 11, 1995 (GB) .............................. 9509557

(51) Int. Cl.[7] .................... A61K 38/08; A61K 38/10
(52) U.S. Cl. .................... 530/328; 530/326; 514/13; 514/15; 514/16; 435/7.1
(58) Field of Search ................. 530/328, 326; 514/16; 435/7.1

(56) References Cited

U.S. PATENT DOCUMENTS

| 5,424,400 A | 6/1995 | Smith |
| 5,596,079 A | 1/1997 | Smith et al. |

FOREIGN PATENT DOCUMENTS

| FR | A-26626983 | 12/1991 |
| WO | WO93/12251 | 6/1993 |
| WO | WO94/09135 | 4/1994 |
| WO | WO95/06415 | 3/1995 |
| WO | WO 96/14334 | 5/1996 |

OTHER PUBLICATIONS

Database CaPlus, DN 122:283591. Hiraoka et al. Genomics, vol. 25(1), 220–5, Jan. 1995.*

Chen, Junjie et al., (1995) "Separate Domains of p21 Involved In The Inhibition of Cdk Kinase and PCNA" Nature, vol. 374, pp. 386388.

Deng, Chuxia, et al., (1995) "Mice Lacking p21[CIP1/WAF1] Undergo Normal Development, but Are Defective In G1 Checkpoint Control" Cell, vol. 82, pp. 675–684.

Eastham, James A., et al. (1995) "In Vivo Gene Therapy with p53 or p21 Adenovirus for Prostate Cancer" Cancer Research, vol. 55, pp. 5151–5155.

El–Deiry, Wafik S., et al., (1993) "WAF1, a Potential Mediator of p53 Tumor Suppression" Cell, vol. 75, pp. 817–825.

(List continued on next page.)

Primary Examiner—Michael Borin
(74) Attorney, Agent, or Firm—LaHive & Cockfield, LLP; Giulio A. DeConti, Jr.; Cynthia L. Kanik (57) ABSTRACT

Fragments of Fen1 that interact with PCNA are disclosed, together with the use of such fragments or mimetics of Fen1 in methods of screening for compounds useful in treating disorders in which PCNA is implicated. In particular, substances which have the property of binding to PCNA are disclosed, said substances comprising:

(i) a fragment of the Fen1 protein containing a peptide of 89 amino acids from the C-terminal region or an active portion thereof; or, (ii) a fragment of the Fen1 protein containing the sequence motif QGRLDxFF; or, (iii) a functional mimetic of said protein fragments;

where "x" is preferably the selected form the amino acids S, D or G.

18 Claims, 4 Drawing Sheets

OTHER PUBLICATIONS

Flores–Rozas, Hernan, et al., (1994) "Cdk–interacting Protein 1 Directly Binds with Proliferating Cell Nuclear Antigen and Inhibits DNA Replication Catalyzed by the DNA Polymerase δ Holoenzyme" Proc. Natl. Acad. Sci. USA, vol. 91, pp. 8655–8659.

Goubin, Francoise and Ducommun, Bernard, (1995) "Identification of Binding Domains on the p21Cip1 Cyclin–dependent Kinase Inhibitor" Oncogene, vol. 10, pp. 2281–2287.

Gu, Yong, et al., (1993) "Inhibition of CDK2 Activity In Vivo By An Associated 20K Regulatory Subunit" Nature, vol. 366, pp. 707–710.

Harper, J. Wade, et al., (1995) "Inhibition of Cyclin–dependent Kinases by p21" Molecular Biology of the Cell, vol. 6, pp. 387–400.

Luo, Yan, et al., (1995) "Cell–cycle Inhibition by Independt CDK and PCNA Binding Domains in $p21^{cip1}$" Nature, vol. 375, pp. 159–161.

MacLachlan, Timothy K., et al.,(1995) "Cyclins, Cyclin–Dependent Kinases and Cdk Inhibitors: Implications in Cell Cycle Control and Cancer" Critical Reviews in Eukaryotic Gene Expression, vol. 5(2), pp. 127–156.

Nakanishi, Makoto, et al. (1995) "Identification of the Active Region of the DNA Synthesis Inhibitory Gene $p21^{Sdi1/CIP1/WAF1}$" The EMBO Journal, vol. 14(3), pp. 555–563.

Nakanishi, Makoto, et al. (1995) "The C–terminal Region of p21SDI1/WAF1/CIP1 Is Involved in Proliferating Cell Nuclear Antigen Binding but Does Not Appear to Be Required for Growth Inhibition" The Journal of Biological Chemistry, vol. 270(29), pp. 17060–17063.

Su, Jin–Yuan, et al. (1995) "Cloning and Characterization of the Xenopus Cyclin–dependent Kinase Inhibitor $p27^{XIC1}$" Proc. Natl. Acad. Sci. USA, vol. 92, pp. 10187–10191.

Waga, Shou, et al., (1994) "The p21 Inihibitor of Cyclin–dependent Kinases Controls DNA Replication by Interaction with PCNA" Nature, vol. 369, pp. 574–578.

Waldman, Todd, et al., (1995) "p21 Is Necessary for the p53–mediated $G_1$ Arrest in Human Cancer Cells" Cancer Research, vol. 55, pp. 5187–5190.

Zhang, Hui, et al., (1994) "p21–containing Cyclin Kinases Exist In Both Active and Inactive States" Genes & Development, vol. 8, pp. 1750–1758.

Harper, J. et al. (1993) The p21 Cdk–Interacting Protein Cip1 Is A Potent Inhibitor of G1 Cyclin–Dependent Kinases Cell, vol. 75 pp. 805–816.

Hiraoka, Lea et al. (1995) "Sequence of Human FEN–1, A Structure–Specific Endonuclease, and Chromosomal Localization of the Gene (FEN1) In Mounse and Human " Genomics 25, pp. 220–225.

Warbrick, Emma et al. (1995) "A Small Peptide Inhibitor of DNA Replication Defines The Site of Interaction Between The Cyclin–Dependent Kinase Inhibitor $p21^{-WAF1}$ And Proliferating Cell Nuclear Antigen" Current Biology, vol. 5 No. 3 pp. 275–282.

Xlong, Yue et al. (1993) "p21 Is A Universal Inhibitor of Cyclin Kinases" Nature, vol. 366, pp. 700–701.

* cited by examiner

Figure 1

| Peptide no. | Sequence | Identity |
|---|---|---|
| 84 | KRLSKSRQGSTQGRLDDFFK (SEQ ID NO:4) | Fen1 amino acids 326-345 |
| 85 | SRQGSTQGRLDDFFKVTGSL (SEQ ID NO:5) | Fen1 amino acids 331-350 |
| 86 | TQGRLDDFFKVTGSLSSAKR (SEQ ID NO:6) | Fen1 amino acids 336-355 |
| 92 | ASKTIPQGRLDSFFKPVPSS (SEQ ID NO:7) | S. pombe rad2 amino acids 332-351 |
| 93 | GLKSGIQGRLDGFFQVVPKT (SEQ ID NO:8) | S. cerevisiae RAD27 amino acids 334-353 |
| Consensus | QGRLDxFF (SEQ ID NO:1) | proposed PCNA binding motif |
| p21PBP | KRRQTSMTDFYHSKRRLIFS (SEQ ID NO:9) | p21$^{Cip1}$ amino acids 141-160 |

```
                           SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
         (A) LENGTH: 8 amino acids
         (B) TYPE: amino acid
         (D) TOPOLOGY: linear (ii) MOLECULE TYPE: peptide (v) FRAGMENT TYPE: internal
```

(ix) FEATURE:
            (A) NAME/KEY: Modified-site
            (B) LOCATION: 6
            (D) OTHER INFORMATION: /note= "Xaa may be any amino acid"

(xi) SEQUENCE DESCRIPTION: SEQ ID NO: 1:

Gln Gly Arg Leu Asp Xaa Phe Phe
 1               5

(2) INFORMATION FOR SEQ ID NO: 2:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 2:

Gln Thr Ser Met Thr Asp Phe Tyr His
 1               5

(2) INFORMATION FOR SEQ ID NO: 3:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 3:

Ser Gly Ser Gly
 1

(2) INFORMATION FOR SEQ ID NO: 4:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 4:

Lys Arg Leu Ser Lys Ser Arg Gln Gly Ser Thr Gln Gly Arg Leu Asp
 1               5                  10                  15

Asp Phe Phe Lys
            20

(2) INFORMATION FOR SEQ ID NO: 5:

(i) SEQUENCE CHARACTERISTICS:
            (A) LENGTH: 20 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO: 5:

```
Ser Arg Gln Gly Ser Thr Gln Gly Arg Leu Asp Asp Phe Phe Lys Val
 1               5                  10                  15

Thr Gly Ser Leu
            20

(2) INFORMATION FOR SEQ ID NO: 6:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 6:

Thr Gln Gly Arg Leu Asp Asp Phe Phe Lys Val Thr Gly Ser Leu Ser
 1               5                  10                  15

Ser Ala Lys Arg
            20

(2) INFORMATION FOR SEQ ID NO:7:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 7:

Ala Ser Lys Thr Ile Pro Gln Gly Arg Leu Asp Ser Phe Phe Lys Pro
 1               5                  10                  15

Val Pro Ser Ser
            20

(2) INFORMATION FOR SEQ ID NO: 8:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 8:

Gly Leu Lys Ser Gly Ile Gln Gly Arg Leu Asp Gly Phe Phe Gln Val
 1               5                  10                  15

Val Pro Lys Thr
            20

(2) INFORMATION FOR SEQ ID NO:9:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 9:
```

-continued

```
Lys Arg Arg Gln Thr Ser Met Thr Asp Phe Tyr His Ser Lys Arg Arg
  1               5                  10                  15
Leu Ile Phe Ser
             20

(2) INFORMATION FOR SEQ ID NO: 10:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO: 10:

Thr Gln Gly Arg Leu Asp Asp Phe Phe Lys
  1               5                  10
```

PCNA BINDING SUBSTANCE

FIELD OF THE INVENTION

The present invention relates to the area of cancer therapeutics. More particularly, the present invention relates to fragments of Fen1 that interact with PCNA, and the use of such fragments or mimetics of Fen1 in methods of screening for compounds useful in treating disorders in which PCNA is implicated.

BACKGROUND OF THE INVENTION

Maintenance of genomic integrity within the cell requires a co-ordination between cell-cycle regulated DNA replication, and DNA repair. In the presence of damaged DNA, proliferating cells must cease DNA replication, so that lesions do not become fixed, and repair all damage before replication can recommence. Therefore, the co-ordination of these two processes is critical to avoid mutation and genomic instability. One protein known to be involved in both in DNA replication and in nucleotide excision repair is proliferating cell nuclear antigen (PCNA).

In solution, PCNA from *Saccharomyces cerevisiae* is thought to exist as a trimer. Each monomer has two structurally similar domains separated by a central loop, and so the trimer shows overall six-fold symmetry, as determined by X-ray crystallographic analysis (Kong et al., 1992; Krishna et al., 1994). Despite variation at the amino acid level, human PCNA is thought to be highly homologous at the structural level to budding yeast PCNA (Krishna et al., 1994). These structural studies have shown that trimeric PCNA forms a toroidal structure around DNA, confirming earlier biochemical studies that suggested that PCNA acts as a sliding clamp around double stranded DNA (reviewed by Kuriyan & O'Donnell, 1993), holding the DNA replication machinery onto its template and thereby greatly enhancing its processivity (Bravo et al., 1987; Prelich et al., 1987b). PCNA is localised to sites of DNA synthesis within the nucleus (eg Bravo & MacDonald-Bravo, 1985), and is required to reconstitute SV40 DNA replication in vitro from purified proteins (Prelich et al., 1987a), clearly demonstrating a requirement for the protein in DNA replication. Similarly, the *Schizosaccharomyces pombe* PCNA gene pcn1 is essential, with cells showing a phenotype characteristic of a defect in DNA replication when pcn1 is deleted (Waseem et al., 1992). In addition to its replication role, PCNA is also required for nucleotide excision repair in cell-free systems (Shivji et al., 1992). However, the way in which PCNA carries out these two separate roles is as yet unclear.

SUMMARY OF THE INVENTION

The present invention is based on the finding that a human protein Fen1 interacts with PCNA. This was shown using a yeast two hybrid screen for proteins encoded by a human cDNA library that interact with human PCNA in a cellular environment.

Fen1 has previously been described as a structure-specific endonuclease (Harrington & Lieber, 1994a) with 5'→3' exonuclease activity (Robins et al., 1994) that shares homology with putative nucleotide excision repair factors including human xeroderma pigmentosum complementation G group protein (Harbraken et al., 1994; O'Donovan et al., 1994), *S. pombe* rad 2 and rad13 (Carr et al., 1993; Murray et al., 1994), and *S. cerevisiae* RAD27/YKL510 and RAD2 (Jacquier et al., 1992; Siede & Friedberg, 1992). The same protein has, however, been identified as an essential DNA replication factor MF1 (Waga et al., 1994a).

The present invention further relates to the characterisation of the interaction between Fen1 and PCNA at the amino acid level by mapping of the mutual binding sites of each protein. This revealed that $p21^{Cip1}$ (also known as $p21^{WAF}1$ or Sdi1), the cyclin-kinase inhibitor that also blocks PCNA's function in DNA replication (Flores et al., 1994; Waga et al., 1994b; Warbrick et al., 1995) but not repair (Li et al., 1994; Shivji et al., 1994), binds to the same site on PCNA as does Fen1. The regions of Fen1 and $p21^{Cip1}$ that interact with PCNA are shown to be homologous, and $p21^{Cip1}$ peptides are found to compete with Fen1 for binding to PCNA.

The finding that $p21^{Cip1}$, or fragments thereof, compete with Fen1 for PCNA, in particular the region of $p21^{Cip1}$ identified in our copending application number PCT/GB95/02583 as being responsible for PCNA binding, leads to the possibility of using Fen1 in the screening of mimetics for $p21^{Cip1}$, in particular those which may block or inhibit cellular DNA replication.

Accordingly, in one aspect, the present invention provides a substance which has the property of binding to PCNA, said substance comprising:

(i) a fragment of the Fen1 protein containing a peptide of 89 amino acids from the C-terminal region or an active portion thereof; or, (ii) a fragment of the Fen1 protein containing the sequence motif QGRLDxFF (SEQ ID NO:1); or (iii) a functional mimetic of said protein fragments.

We have found that "x" may be S, D or G, but probably other amino acids will be tolerated as well.

In the present invention, "an active portion" means a peptide which is less than said full length Fen1 amino acid sequence, but which retains the property of binding to PCNA.

In the present invention, "functional mimetic" means a substance which may not be a peptide at all, but which has the property of binding to PCNA, excluding the $p21^{Cip1}$ fragments disclosed in our earlier application.

In a further aspect, the present invention provides assays using a binding agent which is a fragment or mimetic of Fen1 as described above. In particular, the present invention provides a method of screening for Fen1 or $p21^{Cip1}$ mimetics comprising exposing Fen1 or a fragment or mimetic thereof which binds PCNA (herein referred to as "the Fen1 component") and a candidate mimetic to PCNA or an active fragment thereof (herein referred to as "the PCNA component"), so that the candidate mimetic and the Fen1 component compete to bind the PCNA component, and detecting the extent of binding of the PCNA component to the candidate mimetic and/or the Fen1 component. Candidate mimetics which are found to bind to PCNA can then be further screened for biological activity, especially inhibition of DNA synthesis or inhibition of (tumour) cell growth.

Conveniently, the screening method can be carried out by immobilising the fragment or mimetic of Fen1 on a solid support, and exposing the immobilised Fen1 component to PCNA and various concentrations of the candidate mimetic. The extent of PCNA binding to immobilised Fen1 can be measured using an antibody which detects PCNA. Alternatively, interaction of radiolabelled PCNA with immobilised Fen1 component in the presence of candidate mimetic can be measured in a scintillation proximity assay. Other assay formats and screening techniques using Fen1 fragments or mimetics can be readily determined by the skilled person and used to screen candidate mimetics.

In a further aspect, the present invention includes mimetics obtained by using the above screening method.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, eg peptides may be unsuitable active agents for oral compositions as they tend to be quickly degraded by proteases in the alimentary canal.

There are several steps commonly taken in the design of a mimetic from a compound having a given target property. Firstly, the particular parts of the compound that are critical and/or important in conferring the target property are determined. In the case of a peptide, this can be done by systematically varying the amino acid residues in the peptide, eg by substituting each residue in turn. These parts or residues constituting the active region of the compound are known as its "pharmacophore".

Once the pharmacophore has been found, its structure is modelled according to its physical properties, eg stereochemistry, bonding, size and/or charge, using data from a range of sources, eg spectroscopic techniques such as NMR, X-ray diffraction data, etc. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and has the desired degradation profile in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vitro, in vivo or clinical testing.

The final mimetic may have clinical utility, or it may be useful as a drug in a laboratory setting. In clinical uses, the desired degradation profile may be one in which degradation is minimised, but there are situations where an appropriate rate of degradation is not only desired, but is actually important. For example, the p21$^{Cip1}$ mimetic could be used as a short half-life adjunct to arrest cell proliferation transiently in normal cells while administering genotoxic compounds to cells that override the p21$^{Cip1}$ arrest, for example cancer cells which contain abnormally high levels of PCNA.

Thus, in another aspect, the present invention provides the class of peptides, and also mimetics obtained as described above, based on the PCNA-binding region of Fen1. These compounds, and especially the mimetics, may be useful in the preparation of pharmaceuticals for treating conditions in which PCNA is implicated, including hyperproliferative diseases, such as cancer and psoriasis.

Therapeutic applications of the present invention include the administration of the various peptides or mimetics mentioned above. Various methods of administration of the therapeutic agent can be used, following known formulations and procedures. Dosages can be determined by routine experimentation. The administration may be systemic or targeted, the latter employing direct (eg topical) application of the therapeutic agent to the target cells or the use of targeting systems such as cell type specific antibodies or ligands. Targeting is generally preferable since it minimises or localises any side effects; and may be particularly important for example if the agent is unacceptably toxic when administered systemically, or if it would otherwise require too high a dosage, or if it would not otherwise be able to enter the target cells.

Instead of administering these agents directly, they could be produced in the target cells by expression from an encoding gene introduced into the cells, eg in a viral vector (a variant of the VDEPT technique—see below). The vector could be targeted to the specific cells to be treated, or it could contain regulatory elements which are switched on more or less selectively within the target cells.

Alternatively, the agent could be administered in a precursor form, for conversion to the active form by an activating agent produced in, or targeted to, the cells to be treated. This type of approach is sometimes known as ADEPT or VDEPT; the former involving targeting the activating agent to the cells by conjugation to a cell type specific antibody, while the latter involves producing the activating agent, eg an enzyme, by expression from encoding DNA in a viral vector (see for example, EP-A-415731 and WO 90/07936).

In a further aspect, the present invention identifies the region of PCNA involved in binding to Fen1. Thus, the present invention provides a substance which has the property of binding to Fen1, said substance comprising a fragment of PCNA lying between amino acids 100–150, or an active portion thereof; or a functional mimetic of said protein fragments.

If fragments of PCNA in this region retain the ability to bind to p21$^{Cip1}$ or Fen1, it may be possible to use these: (i) to regulate p21$^{Cip1}$ dosage, (ii) to screen for Fen1 or p21$^{Cip1}$ mimetics and in the design of substances to bind to this site in PCNA; (iii) to induce proliferation in hypoproliferative cells, for example to reactivate senescent cells.

BRIEF DESCRIPTION OF THE DRAWINGS

FIG. 2 shows sequences also shown in SEQ ID NO:4, SEQ ID NO:5, SEQ ID NO: 6, SEQ ID NO:7, SEQ ID NO:8, SEQ ID NO: 1, and SEQ ID NO:9.

FIG. 3 shows the determination of the Fen1 binding site on PCNA. A series of N-terminal and C-terminal deletions of PCNA was constructed in frame with the DNA binding domain of Gal4, and co-expressed in the two hybrid system with Fen1 fused to the transcriptional activation domain of Gal4. Reconstitution of a functional Gal4 transcription factor was scored (ticks) assays for β-galactosidase or His3 activity. An entire PCNA monomer is shown schematically, with structural domains and motifs designated as described by Krishna et al. (1994). In a parallel series of experiments, interaction of p21$^{Cip1}$ with the PCNA constructs was assayed. Note that Fen1 and p21$^{Cip1}$ show an identical pattern of binding to the PCNA constructs, localising the binding site for each protein in the central 100–150 amino acids of PCNA, including the exposed loop between βI$_1$ of domain 1 and βA$_2$ –αA$_2$ of domain 2.

DETAILED DESCRIPTION

Yeast Two Hybrid Screen and Construction of Deletions

The two hybrid screen and deletion analysis was carried out essentially as described previously (Warbrick et al., 1995, and International patent application PCT/GB95/02583).

Further constructs were made by subcloning fragments from the human PCNA open reading frame into pAS2.

Protein Precipitation and Western Blotting

Twenty amino acid peptides with 15 amino acid overlaps were synthesized (Chiron Mimotopes, Australia) across the 89 amino acids from the C-terminal region of Fen1 identified in the two hybrid screen as the PCNA binding site on Fen1. These peptides were linked via residues SGSG (SEQ ID NO:3) at the amino acid terminus to biotin. 2.7 µg of each peptide was incubated with 10 µl streptavidin agarose beads (Sigma) in phosphate buffered saline (PBS) for 1 hour at room temperature (r.t.) then beads were washed extensively in PBS and recovered each time by centrifugation at 11,600 g. HeLa cell lysate was added to the washed beads to a final protein concentration of 1 mg/ml and incubated with the beads on ice for 1 hour. Beads were extensively washed in PBS with 220 mM NaCl, then bound proteins removed by boiling for 8 minutes in SDS loading buffer with 0.2 M DTT. Proteins were separated on 10% SDS-PAGE then electrophoretically transferred to nitrocellulose. Blots were blocked then incubated for 1 hour r.t. with PC 10 hybridoma supernatant (Waseem & Lane, 1990) diluted 1:5 in DMEM with 10% FCS. After washing, secondary HRP-conjugated anti-mouse IgG serum at 1:1000 in 2% non-fat milk-PBS-0.2% Tween was added for 1 hour at r.t. Bound antibody was visualised using the ECL system according to the manufacturer's instructions (Amersham plc.)

Competitive ELISA

Figure 2:
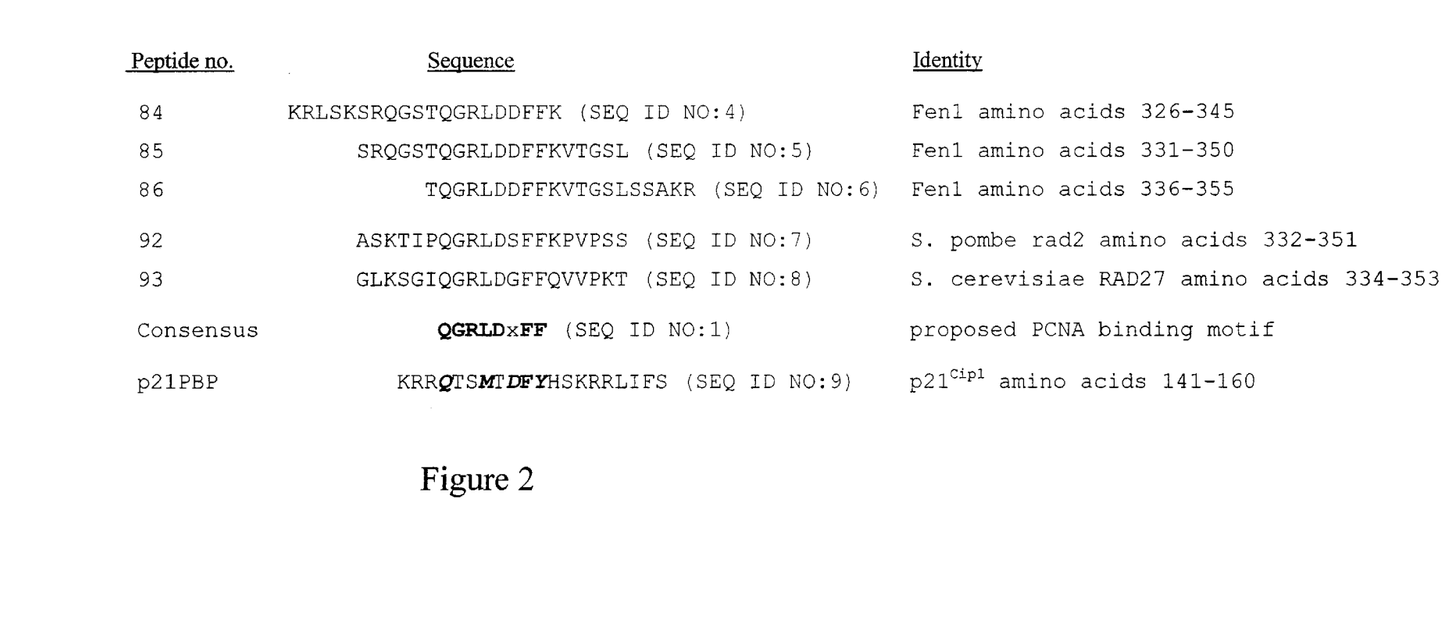
FIG. 2 shows the conservation of the PCNA binding site between Fen1 homologues. The sequences of peptides that bound to PCNA in a precipitation assay (see below) are aligned, giving a consensus sequence of QGRLDxFF (SEQ ID NO: 1). Conservation of critical residues with the PCNA binding site on p21$^{Cip1}$ is shown in bold type.

ELISA plates were coated overnight at 37° C. with 100 ng of streptavidin per well. Plates were blocked with 5% non-fat milk powder in PBS, washed extensively with PBS containing 0.2% Tween 20 (PBS-T) then 100 µl FenPBP—peptide 84 (SEQ ID NO:4) (see FIG. 2)—at 10 µg/ml was added to each well. Following 1 hour incubation at r.t. in a humid chamber, wells were washed extensively. Approximately 3.5 µg total protein containing overexpressed recombinant human PCNA was mixed with varying concentrations of a 9 amino acid peptide derived from p21PBP (Warbrick et al, 1995), of the sequence QTSMTDFYH (SEQ ID NO:2) (purified by HPLC and verified by mass spectrometry) and applied to the wells for 1 hour at r.t. After extensive washing, anti-PCNA polyclonal antibody 3009 (Cox et al., manuscript in preparation) was added at 1:1000, followed by HRP-conjugated anti-rabbit IgG serum at 1:1000, and bound antibody was visualized by the TMB colormetric procedure (Harlow & Lane, 1998). Plated were read at 450 nm using a Dynatech 5000 plate reader.

Results

The 89 Amino Acids From the C-terminal Region of Fen1 Bind PCNA in an Interaction Trap Proteins that interact physically with human PCNA were screened using a two hybrid interaction trap system that detects protein-protein interactions by reconstitution of a functional Gal4 transcriptional activator in the yeast *Saccharomyces cerevisiae*. A plasmid expressing human PCNA in fusion with the DNA binding domain of Gal4 (Gal4AS) was used to screen plasmids expressing fusion constructs of molecules encoded by fragments from a human cDNA library with the transcriptional activation domain of Gal4 (Gal4ACT). On DNA sequencing, one class of clones isolated by this screen was found to encode fragments of the human protein Fen1 (Harrington & Lieber, 1994a; Harrington & Lieber, 1994b), also known as DNase IV (Robins et al., 1994), rad2hs (Murray et al., 1994) and MF1 (Waga et al., 1994a). The minimal Fen1 fragment isolated in our screen (FIG. 1) encoded the 89 amino acids from the C-terminal region of the protein (full length 380 aa, (Murray et al., 1994)), therefore localising the PCNA binding site to these residues. PCNA from Drosophila melanogaster and Schizosaccharomyces pombe also interacted in this system with human Fen1, suggesting strong evolutionary conservation of the interaction site on PCNA.

Peptide Mapping of Sites on Fen1 Important for Interaction With PCNA

Figure 1:
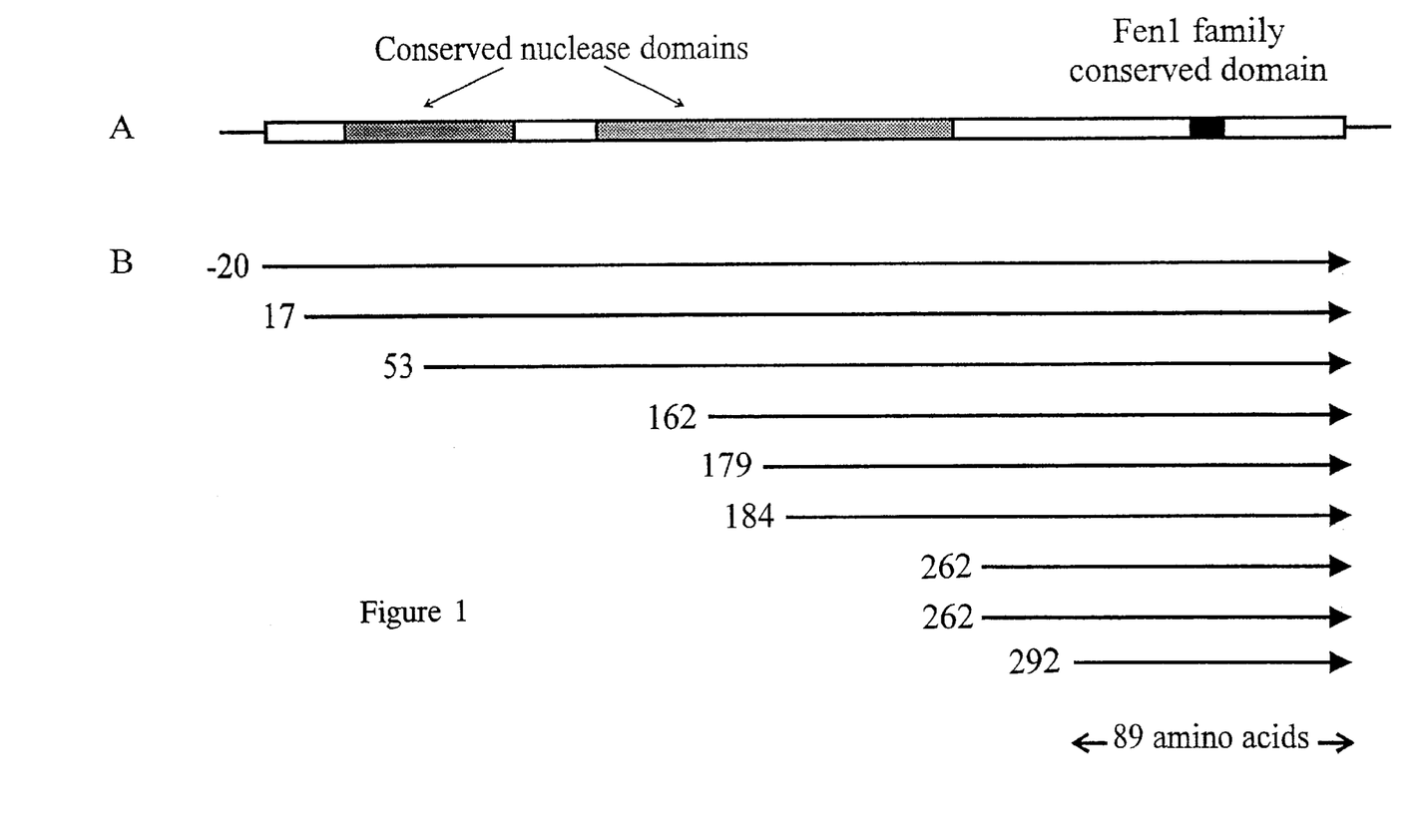
FIG. 1 shows human Fen1 and fragments isolated in the yeast two hybrid screen by interaction with human PCNA. (A) Schematic diagram of Fen1, showing the conserved nuclease domains, and the carboxy terminal Fen1 box, conserved throughout the Fen1 family. (B) Nine plasmids encoding Fen1 fragments were isolated in the yeast two hybrid screen, encoding full length Fen1 and various fragments truncated at the amino terminus. The shortest fragment isolated contained 89 amino acids from the C-terminal region of Fen1.

To map precisely the residues of Fen1 to which PCNA binds, a series of biotinylated 20 amino acids peptides (with 15 amino acid overlaps) were synthesized representing the region of Fen1 found to interact with PCNA in the two hybrid screen (FIG. 1). Fen1 peptides (bound to streptavidin agarose beads) were incubated with human HeLa cell extracts, then beads were precipitated and bound protein analysed on immunoblots probed with monoclonal anti-PCNA antibody PC10 (Waseen & Lane, 1990). The results showed that PCNA was precipitated from HeLa cell extract with equal efficiency by peptides 84 (SEQ ID NO:4), 85 (SEQ ID NO:5), and 86 (SEQ ID NO:6) (see FIG. 2), strongly suggesting that the amino acids TQGRLDDFFK (SEQ ID NO:10) common to these three Fen1 peptides are important for binding to PCNA. Comparison of the amount of PCNA present in the undepleted extract and that precipitated by Fen1 peptides 84–86 (SEQ ID NOs:4, 5, and 6, respectively) demonstrated quantitative removal of PCNA protein from the whole cell lysate, indicating a high affinity of interaction between PCNA and the Fen1 peptides.

A PCNA-binding Consensus Sequence

The region of human Fen1 recognised by PCNA in the precipitation assay contains a motif highly conserved in the Fen1 family. We examined whether human PCNA could bind to his motif in the yeast homologues of Fen1, *S. pombe* rad2 and *S. pombe* RAD27/YKL510. Biotinylated peptides were synthesized according to the published sequences of *S. pombe* rad 2 (Murray et al., 1994) and *S. cerevisiae* RAD27/YKL510 (Jacquier et al., 1992) in the region homologues to that portion of Fen1 shown to interact with PCNA. These peptides 92 (SEQ ID NO:7) and 93 (SEQ ID NO:8) (see FIG. 2) were used in a precipitation reaction as described above. The PC10 immunoblot of proteins precipitated from HeLa cell extract by 20 amino acid peptides of this conserved box from *S. pombe* (peptide 92) (SEQ ID NO:7) and *S. cerevisiae* (peptide 93) (SEQ ID NO:8) showed that PCNA binds to the conserved region in rad2 and RAD27 with similar affinity to Fen1 peptides 84–86 (SEQ ID NOs:4, 5 and 6, respectively), demonstrating remarkable conservation of the binding motif. Binding of PCNA to the previously defined $p21^{Cip1}$-PCNA binding peptide (p21PBP—Warbrick, 1995) was used as a positive control and streptavidin-agarose beads alone as the negative control. By comparison of the sequences of these PCNA-interacting peptides from diverse species (FIG. 2), we can define a PCNA binding site of QGRLDxFF (SEQ ID NO:1).

Fen1 is most closely homologous to rad2 of *S. pombe* and RAD27/YKL510 of *S. cerevisiae*, but it shares limited homology also with putative nucleotide excision repair-associated proteins rad13 (*S. pombe*), RAD2 (*S. cerevisiae*) and, provocatively, the human xeroderma pigmentosum complementation group G protein. Alignment of these sequences reveals similarity in the region that we find important for Fen1 to bind to PCNA, defining a novel PCNA binding motif. Remarkably, the residues of $p21^{Cip1}$ that we have previously found to be critical for binding to PCNA are very similar to those required by members of the Fen1 family for PCNA interaction.

Fen1 Interacts With the Central Region of PCNA

Figure 3:
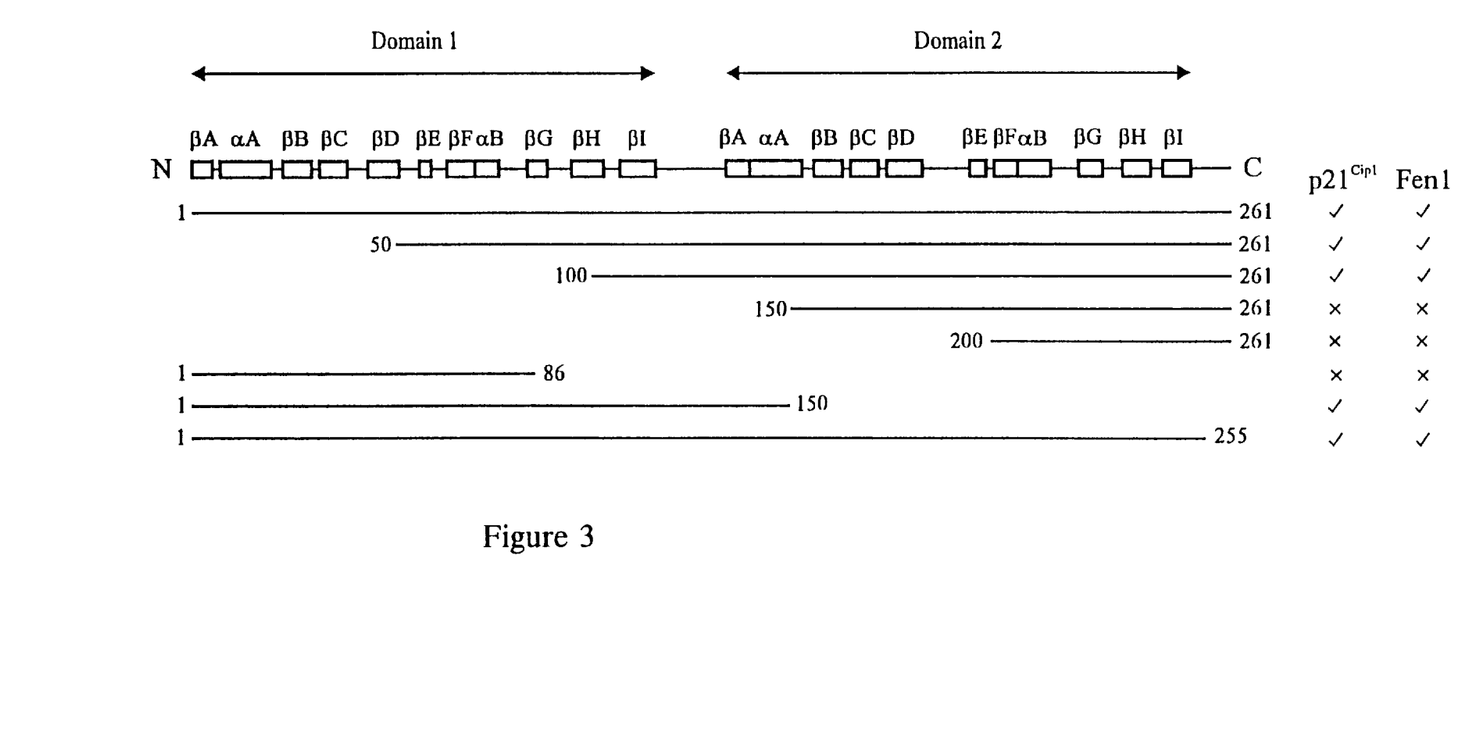
Figure 4:
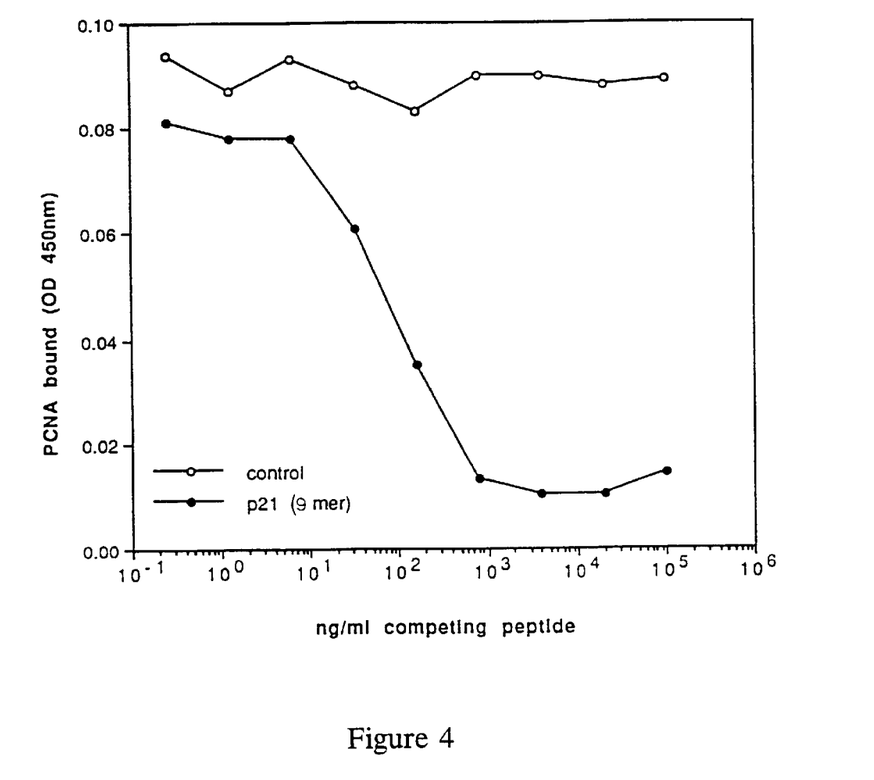
FIG. 4 shows how a short peptide of p21$^{Cip1}$ competes with FenPBP (see below) for binding to PCNA. Biotinylated FenPBP (peptide 84 (SEQ ID NO:4)—see FIG. 2) was immobilised on ELISA dishes pre-coated with streptavidin. Bacterial cell lysate overexpressing recombinant human PCNA was mixed with increasing amounts of a non-biotinylated 9 amino acid peptide QTSMTDFYH (SEQ ID NO:2) derived from p21PBP (Warbrick et al., 1995), then binding of PCNA to the immobilised FenPBP was measured using polyclonal antibody 3009 against PCNA, followed by HRP-anti-rabbit antibody, and calorimetric detection at 450 nm. The p21$^{Cip1}$ peptide at only 1 µg/ml (approximately 1 µM) completely prevented PCNA binding to Fen1PBP.

To define the region of PCNA important for Fen1 binding, we created a series of deletion constructs of PCNA fused to GAl4AS and examined their ability to interact with Fen1 plasmids in the two hybrid system. The results (FIG. 3) show that Fen1 binds to a region between residues 100 and 150 of PCNA. This region corresponds to the central loop of PCNA between the two domains of each monomer, and includes also the structural motifs βI1, βA2 and αA2 (from the crystal structure of *S. cerevisiae* PCNA, (Krishna et al., 1994)). Remarkably, this region has also been implicated in the binding of the cyclin-kinase inhibitor $p21^{Cip1}$ to PCNA (Warbrick et al., 1995) using N-terminal deletions of PCNA. Thus, we confirmed and extended the earlier observations of $p21^{Cip1}$-PCNA interaction in the two hybrid system using the new series of deletion constructs (FIG. 4), and demonstrate that Fen1 and $p21^{Cip1}$ bind to the same region of PCNA.

$p21^{Cip1}$ Competes With Fen1 for Binding to PCNA

Since the region of PCNA bound by Fen1 is the same as that recognised by $p21^{Cip1}$, and the motif of Fen1 required for PCNA interaction appears homologous to the critical residues of p21PBP (Warbrick et al., 1995), it is highly possible that Fen1 and $p21^{Cip1}$ might compete for binding to PCNA. We therefore tested this hypothesis using PCNA-interacting peptide 84 (SEQ ID NO:4) of Fen1 (dubbed Fen1PBP for Fen1-PCNA binding peptide) immobilised in ELISA wells. Recombinant human PCNA was added, together with increasing amounts of a non-biotinylated 9-mer peptide of $p21^{Cip1}$ containing the critical amino acids for PCNA interaction QTSMTDFYH (SEQ ID NO:2), as defined by Warbrick, et al. (1995). This short peptide of $p21^{Cip1}$ clearly competes for PCNA binding to Fen1PBP (FIG. 4), with total displacement of PCNA from immobilised Fen1PBP at only 1 mM added $p21^{Cip1}$ peptide. An irrelevant 20-mer peptide was used to control from non-specific effects of peptides and the solvent DMSO on PCNA binding to Fen1PBP.

Discussion

In this application, we disclose a direct interaction between two proteins implicated in DNA replication and DNA repair; the flap endonuclease Fen1 (Harrington & Lieber, 1994a; Harrington & Lieber, 1994b) [also known as Dnase IV (Robins et al., 1994), rad2hs (Murray et al., 1994) and MF1 (Waga et al., 1994)] and the DNA polymerase δ auxiliary sliding clamp, PCNA (Bravo et al., 1987; Prelich et al., 1987b). Deletion mapping in the two hybrid system permits us to define 89 amino acids of Fen1 as containing the PCNA binding site. Analysis using peptides synthesized according to the shortest Fen1 fragment isolated in the two hybrid screen then allowed us to map the PCNA binding site to three overlapping Fen1-PCNA binding peptides (Fen1 PBPs). Comparison of sequence overlaps in these Fen1 peptides, and those derived from Fen1 homologues in *S. cerevisiae* (YKL5 1I0/RAD27) and *S. pombe* (rad2) defines the PCNA binding region as 8 amino acids: QGRLDxFF (SEQ ID NO: 1). This motif is partially conserved in another family of proteins probably required for nucleotide excision repair that share limited homology with Fen1, including the *S. pombe* rad13 gene product, *S. cerevisiae* RAD2 and the human Xeroderma pigmentosum XP-G protein. Remarkably, residues critical for PCNA binding are shared also with the region of the cyclin-kinase inhibitor, $p21^{Cip1}$, required for interaction with PCNA (Warbrick et al., 1995). Accordingly, this motif may define a novel PCNA binding consensus.

A series of amino terminal and carboxy terminal deletions of PCNA localised the Fen1 binding site to the region between amino acids 100–150, which include residues exposed in a loop between the two domains of each PCNA monomer. Although our data do not yet permit us to define the Fen1 binding site at the level of individual amino acids, it is possible that interaction involves those residues of PCNA most exposed in solution, ie those contained within the 17 amino acids of the loop.

The interaction is conserved across evolution not only for Fen1 homologues, but also for PCNA, since PCNA from *D. melanogaster* and *S. pombe* also bind to fragments of human Fen1 in the two hybrid system. Such a level of conservation suggests that this interaction may be critical for cellular DNA replication and/or repair. We have already shown that this central loop of PCNA may provide a binding site for $p21^{Cip1}$. Since Fen1 and $p21^{Cip1}$ share amino acids essential for PCNA binding, and appear to bind to the same site on PCNA, they should competitively modulate PCNA function, suggesting uses for these proteins in the treatment of cancer and other hyperproliferative disorders.

PCNA is fundamental to nuclear DNA replication, acting as a sliding clamp that tethers the DNA replication machinery to its template, enhancing the enzyme's processivity. In addition, PCNA is required for nucleotide excision repair (Shivji et al., 1992). PCNA may be recruited to these different roles in replication and repair by interaction with proteins specific to each process. Examination of PCNA's partners is therefore a critical goal in the understanding of both DNA repair and DNA synthesis. This work demonstrates an interaction of PCNA with Fen1, a structure-specific endonuclease.

The demonstration of a direct PCNA-Fen1 interaction begs the question of the biological function and activity of such a complex. Two hypotheses are consistent with our data: (1) that the PCNA-Fen1 complex functions in DNA replication; (2) that the complex is active in DNA repair. Does the known activity of Fen1 support either hypothesis? Fen1 protein has been suggested to function in mammalian nucleotide excision repair, because of its homology to known repair gene products. It is a structure-specific flap endonuclease identified as the human homologue of the *S. pombe* rad2 gene product (rad2hs, (Murray et al., 1994), DNase IV, (Robins et al., 1994)). It specifically cuts DNA flaps ending in a 5' single stranded region, requiring the entire flap structure, but acting independently of flap length (Harrington & Lieber, 1994a). In addition, Fen1 possesses 5'→3' exonuclease activity specific for double stranded DNA (Harrington & Lieber, 1994a). Human and mouse Fen1 share homology with structure-specific endonucleases YKL510 (RAD27) and RAD2 from *S. cerevisiae* (Harrington & Lieber, 1994b), and human Xeroderma pigmentosum complementation group G protein (Murray et al., 1994; O'Donovan et al., 1994) also known as ERCC5, (Shiomi et al., 1994). Two UV-inducible upstream elements are present in the promoter of the *S. cerevisiae* RAD2 gene, that show increased protein binding following genotoxic insult, characteristic of a DNA repair gene (Siede & Friedberg, 1992). Interestingly, these two elements DRE1 and DRE2 may be differentially regulated through the cell cycle, since deletion of DRE1 results in increased UV sensitivity only in G1/S, while deletion of DRE2 leads to greater sensitivity in G1/S, S/G2 and in stationary phase (Siede & Friedberg, 1992). Structural and functional homology between Fen1 and characterised repair proteins therefore supports the suggestion that Fen1 is involved in mammalian nucleotide excision repair.

Several lines of evidence, however, point towards an additional role for Fen1 in DNA replication. It is essential for the maturation of replicated SV40 DNA into covalently closed circles (form I), and possesses RNase H activity that may remove ribonucleotide primers from Okazaki fragments (Waga et al., 1994a). The bovine homologue of Fen1 has been detected in partially purified fractions of DNA polymerase ε, and is required for complete DNA synthesis on a synthetic DNA substrate in a lagging strand reaction (Siegal et al., 1992; Turchii & Bambara, 1993). Although identified as radiation-sensitive mutations, the *S. pombe* and *S. cerevisiae* homologues of Fen1 show mutant phenotypes consistent with a fault in DNA replication (eg. Reagan et al., 1995). Provocatively, the upstream region of the *S. cerevisiae* RAD27 gene contains two MluI boxes characteristic of genes whose products are required in S phase, and its transcript reaches maximal levels in G1/S. These features of Fen1 and its homologues are highly consistent with a role in S phase DNA replication. Two alternate roles of the protein in DNA replication and repair are not incompatible, since PCNA, for instance, functions in both processes.

Competition between Fen1 and p21$^{Cip1}$ for PCNA binding may modulate function of the clamp protein, and though we do not wish to be bound by a particular theory, it is provocative to consider the idea that p21$^{Cip1}$ binding to PCNA may shift it from a replication competent form (PCNA-Fen1) to a repair-competent form that cannot support DNA replication. Such an alteration in PCNA function might provide a direct link between the cessation of DNA replication following DNA damage, and the onset of DNA repair. Consistent with this hypothesis, p21$^{Cip1}$ is transcriptionally induced by the human tumour suppressor protein p53 (El-Deiry et al., 1993) which is itself induced in response to genomic damage (reviewed by Cox & Lane, 1995). Coupled with higher levels of p21$^{Cip1}$ following genomic damage, higher affinity of p21$^{Cip1}$ than Fen1 for PCNA might well result in total displacement of Fen1 from the complex.

The results presented here have applications beyond the biological role of PCNA and Fen1 in DNA replication and repair complexes. PCNA is elevated in certain human tumours above the level of other cell cycle markers such as Ki67 (eg. Knechel et al., 1993), and we have already described a peptide of p21$^{Cip1}$, p21PBP, that may be useful in inhibiting PCNA's replication activity in hyperproliferating cells. Development of new drugs that mimic the PCNA-inhibitory activity of p21$^{Cip1}$ requires a suitable screening procedure. Thus, the work described herein in which a minimal peptide derived from p21PBP successfully competes with Fen1PBP for binding to PCNA, can be readily extended to provide a rapid and reproducible screen for small molecules that mimic p21PBP activity in PCNA binding and possibly inhibition of DNA synthesis. Drugs defined by such a screen should prove useful for treatment of hyperproliferative diseases including cancer.

References

Bravo, R., Frank, R., Blundell, P. A. & MacDonald-Bravo, H. (1987). Cyclin/PCNA is the auxiliary protein of DNA polymerase delta. Nature 326, 515–517.

Bravo, R. & MacDonald-Bravo, H. (1985). Changes in the nuclear distribution of cyclin (PCNA) but not its synthesis depend on DNA replication. EMBO J. 4, 655–661.

Carr, A. M., Sheldrick, K. S., Murray, J. M., al-Harithy, R., Watts, F. Z. & Lehmann, A. R. (1993). Evolutionary conservation of excision repair in *Schizosaccharomyces pombe*: evidence for a family of sequences relalted to the *Saccharomyces cerevisiae* RAD2 gene. Nucleic Acids Res. 21, 1345–1349.

Cox, L. S. & Lane, D. P. (1995). Tumour suppressors, kinases and clamps: how p53 regulates the cell cycle in response to DNA damage. BioEssays in press, El-Deiry, W. S., Tokino, T., Velculescu, V. E., Levy, D. B., Parsons, R., Trent, J. M., Lin, D., Mercer, W. E., Kinzler, K. W. & Vogelstein, B. (1993). WAF-1, a potential mediator of p53 tumour suppression. Cell 75, 817–825.

Flores, R. H., Kelman, Z., Dean, F. B., Pan, Z. Q., Harper, J. W., Elledge, S. J., O'Donnell, M. & Hurwitz, J. (1994). Cdk-interacting protein 1 directly binds with proliferating cell nuclear antigen and inhibits DNA replication catalyzed by the DNA polymerase delta holoenzyme. Proc Natl Acad Sci U S A 91, 8655–9.

Harbraken, Y., Sung, P., Prakash, L. & Prakash, S. (1994). A conserved 5' to 3' exonuclease activity in the yeast and human nucleotide excision repair proteins RAD2 and XPG. J. Biol. Chem. 269, 31342–31345.

Harlow, E. & Lane, D. P. (1988). Antibodies. A laboratory manual. (ed. 1 ed. 1 vols. Cold Spring Harbor: Cold Spring Harbor Laboratory. 726.

Harrington, J. J. & Lieber, M. R. (1994a). The characterisation of a mammalian DNA structure-specific endonuclease. EMBO J. 13, 1235–1246.

Harrington, J. J. & Lieber, M. R. (1994b). Functional domains within FEN-1 and RAD2 define a family of structure-specific endonucleases: implications for nucleotide excision repair. Genes Dev. 8, 1344–1355.

Jacquier, A., Legrain, P. & Dujon, B. (1992). Sequence of a 10.7 kb segment of the yeast chromosome XI identifies the APN1 and the BAF1 loci and reveals one tRNA gene and several new open reading frames including homologs to RAD2 and kinases. Yeast 8, 121–132.

Knechel, R., Burgan, M., Rueschoff, J. & Hofstaeder, F. (1993). Proliferating cell nuclear antigen in normal urothelium and urothelial lesions of the urinary bladder: a quantitative assessment using a true colour image analysis system. Virchows Arch. B. Cell Pathol. incl. Mol. Pathol. 64, 137–144.

Kong, X. -P., Onrsut, R., O'Donnell, M. & Kuriyan, J. (1992). Three-dimensional structure of the beat subunit of E. coli DNA polymerase III holoenzyme: a sliding DNA clamp. Cell 69, 425–437.

Krishna, T., Kong, X., Gary, S., Burgers, P. & Kuriyan, J. (1994). Crystal structure of the eukaryotic DNA polymerase processivity factor PCNA. Cell 79, 1233–1243.

Kuriyan, J. & O'Donnell, M. (1993). Sliding clamps of DNA polymerases. J. Mol. Biol. 234, 915–925.

Li, R., Waga, S., Hannon, G. J., Beach, D. & Stillman, B. (1994). Differential effects by the p21 CDK inhibitor on PCNA-dependent DNA replication and repair. Nature 371, 534–537.

Murray, J. M., Tarassoli, M., al-Harithy, R., Sheldrick, K. S., Lehman, A. R., Carr, A. M. & Watts, F. Z. (1994). Structural and functional conservation of the human homologue of the Schizosaccharomyces pombe rad2 gene, which is required for chromosome segregation and recovery from DNA damage. Mol. Cell Biol. 14, 4878–4888.

O'Donovan, A., Davies, A. A., Moggs, J. G., West, S. C. & Wood, R. D. (1994). XPG endonuclease makes the 3' incision in human DNA nucleotide excision repair. Nature 371, 432–435.

Prelich, G., Kostura, M., Marshak, D. R., Mathews, M. B. & Stillman, B. (1987a). The cell-cycle regulated proliferating cell nuclear antigen is required for SV40 DNA replication in vitro. Nature 326, 471–475.

Prelich, G., Tan, C. K., Kostura, M., Mathews, M. B., So, A. G., Downey, K. M. & Stillman, B. (1987b). Functional identity of proliferating cell nuclear antigen and a DNA polymerase delta auxiliary protein. Nature 326, 517–520.

Reagan, M. S., Pittenger, C., Siede, W. & Friedberg, E. C. (1995). Characterisation of a mutant strain of Saccharomyces cerevisiae with a deletion of the RAD27 gene, a structural homolog of the RAD2 nucleotide excision repair gene. J. Bact. 177, 364–371.

Robins, P., Pappin, D. J., Wood, R. D. & Lindahl, T. (1994). Structural and functional homology between mammalian DNase IV and the 5'-nuclease domain of Escherichia coli DNA polymerase I. J. Biol. Chem. 269, 28535–28538.

Shiomi, T., Harada, Y., Saito, N., Okuno, Y. & Yamaizumi, M. (1994). An ERCC5 gene with homology to yeast RAD2 is involved in group G xeroderma pigmentosum. Mutat. Res. 314, 167–175.

Shivji, M. K. K., Grey, S. J., Strausfeld, U. P., Wood, R. D. & Blow, J. J. (1994). Cip1 inhibits DNA replication but not PCNA-dependent nucleotide excision repair. Curr. Biol. 4, 1062–1068.

Shivji, M. K. K., Kenny, M. K. & Wood, R. D. (1992). Proliferating cell nuclear antigen is required for DNA excision repair. Cell 69, 367–374.

Siede, W. & Friedberg, E. C. (1992). Regulation of the yeast RAD2 gene: DNA damage-dependent induction correlates with protein binding to regulatory sequences and their deletion influences survival. Mol. Gen. Genet. 232, 247–256.

Siegal, G., Turchii, J. J., Myers, T. W. & Bambara, R. A. (1992). a 5' to 3' exonuclease functionally interacts with calf polymerase e. Proc. Natl. Acad. Sci. 89, 9377–9381.

Turchii, J. J. & Bambara, R. A. (1993). Completion of mammlian lagging strand DNA replciation using purified proteins. J. Biol. Chem. 268, 15136–15141.

Waga, S., Bauer, G. & Stillman, B. (1994a). Reconstitution of complete SV40 DNA replication with purified replication factors. J. Biol. Chem. 269, 10923–10934.

Waga, S., Hannon, G. J., Beach, D. & Stillman, B. (1994b). The p21 inhibitor of cyclin-dependent kinases controls DNA replication by interaction with PCNA [see comments]. Nature 369, 574–8.

Warbrick, E., Lane, D. P., Glover, D. M. & Cox, L. S. (1995). A small peptide inhibitor of DNA replication defines the site of interaction between the cyclin-kinase inhibitor p21WAF1 and proliferating cell nuclear antigen. Current Biology 5, 275–282.

Waseem, N., Labib, K., Nurse, P. & Lane, D. P. (1992). Isolation and analysis of the fission yeast gene encoding polymerase delta accessory protein PCNA. EMBO J. 11, 5111–5120.

Waseem, N. H. & Lane, D. P. (1990). Monoclonal antibody analysis of the proliferating cell nuclear antigen (PCNA). Structural conservation and the detection of a nucleolar form. J. Cell Sci. 96, 121–129.

What is claimed is:

1. A fragment of a human Fen1 protein comprising the amino acid sequence QGRLDxFF (SEQ ID NO:1), where "x" is selected from the group consisting of S, D and G.

2. The fragment of claim 1, wherein the fragment comprises the C-terminal 89 amino acids of the human Fen1 protein.

3. The fragment of claim 1, wherein the fragment comprises at least 20 amino acids of the human Fen1 protein.

4. The fragment of claim 1, comprising the amino acid sequence TQGRLDDFFK (SEQ ID NO:10).

5. The fragment of claim 1, comprising the amino acid KRLSKSRQGSTQGRLDDFFK (SEQ ID NO:4).

6. The fragment of claim 1, comprising the amino acid sequence SRQGSTQGRLDDFFKVTGSL (SEQ ID NO:5).

7. The fragment of claim 1, comprising the amino acid sequence TQGRLDDFFKVTGSLSSAKR (SEQ ID NO:6).

8. A fragment of a human Fen1 protein comprising the amino acid sequence QGRLDxFF (SEQ ID NO:1), wherein "x" is S.

9. A fragment of a human Fen1 protein comprising the amino acid sequence QGRLDxFF (SEQ ID NO:1), wherein "x" is G.

10. A fragment of a human Fen1 protein comprising the amino acid sequence QGRLDxFF (SEQ ID NO:1), wherein "x" is D.

11. A polypeptide comprising a fragment derived from the C-terminal 89 amino acids of human Fen1, wherein the polypeptide binds to PCNA.

12. A composition comprising the fragment of claim 1 and a pharmaceutically acceptable carrier.

13. A composition comprising the fragment of any of claims 2–7 and a pharmaceutically acceptable carrier.

14. A method of screening for Fen1 or p21$^{Cip1}$ mimetics comprising contacting the fragment of claim 1 and a candidate mimetic with PCNA, or an active fragment thereof, so that the candidate mimetic and the fragment compete for binding to the PCNA component, and detecting binding of the PCNA component to the candidate mimetic or the fragment.

15. The method of claim 14 further comprising screening the candidate mimetics for a biological activity.

16. The method of claim 15 wherein the biological activity is the inhibition of DNA synthesis or inhibition of tumor cell growth.

17. The method of claim 14 wherein the fragment or the candidate mimetic is immobilized on a solid support.

18. The method of claim 14 wherein the extent to binding of the candidate mimetic is detected by labeling the PCNA or active fragment thereof or by using a labeled antibody capable of binding to PCNA.

* * * * *